United States Patent
Lemonds et al.

(10) Patent No.: US 9,199,910 B2
(45) Date of Patent: Dec. 1, 2015

(54) PROCESS FOR PRODUCTION OF METHACRYLIC ACID ESTERS

(71) Applicant: Rohm and Haas Company, Philadelphia, PA (US)

(72) Inventors: Andrew M. Lemonds, Schwenksville, PA (US); Jinsuo Xu, Fort Washington, PA (US)

(73) Assignee: Rohm and Haas Company

( * ) Notice: Subject to any disclaimer, the term of this patent is extended or adjusted under 35 U.S.C. 154(b) by 0 days.

(21) Appl. No.: 14/398,767

(22) PCT Filed: May 21, 2013

(86) PCT No.: PCT/US2013/041970
§ 371 (c)(1),
(2) Date: Nov. 4, 2014

(87) PCT Pub. No.: WO2013/184345
PCT Pub. Date: Dec. 12, 2013

(65) Prior Publication Data
US 2015/0141694 A1    May 21, 2015

Related U.S. Application Data

(60) Provisional application No. 61/655,175, filed on Jun. 4, 2012.

(51) Int. Cl.
*C07C 67/327*  (2006.01)

(52) U.S. Cl.
CPC .................................. *C07C 67/327* (2013.01)

(58) Field of Classification Search
CPC .................................................. C07C 67/327
See application file for complete search history.

(56) References Cited

U.S. PATENT DOCUMENTS

| | | |
|---|---|---|
| 3,487,101 A | 12/1969 | Volker et al. |
| 4,464,539 A | 8/1984 | Hashimoto et al. |
| 4,529,816 A | 7/1985 | DeColibus et al. |
| 4,801,571 A | 1/1989 | Montag et al. |
| 4,841,060 A | 6/1989 | Hino et al. |
| 5,068,399 A | 11/1991 | Naito et al. |
| 5,250,729 A | 10/1993 | Abe et al. |
| 5,304,656 A | 4/1994 | Yano et al. |
| 5,371,273 A | 12/1994 | Shima et al. |
| 5,393,918 A | 2/1995 | Dobson |
| 5,625,076 A | 4/1997 | Shimasaki et al. |
| 5,739,379 A | 4/1998 | Shima et al. |
| 6,544,924 B1 | 4/2003 | Jackson et al. |
| 9,000,211 B2 | 4/2015 | Lemonds et al. |
| 2002/0055650 A1 | 5/2002 | Hidaka et al. |

FOREIGN PATENT DOCUMENTS

| | | | |
|---|---|---|---|
| FR | 2064583 | | 6/1971 |
| GB | 409733 | | 10/1938 |
| GB | 1256288 | | 12/1971 |
| JP | 4420611 | | 9/1969 |
| JP | 4420612 | | 9/1969 |
| JP | 4515724 | | 6/1970 |
| JP | 5210214 | | 1/1977 |
| JP | 03264551 | | 11/1991 |
| WO | WO 2012/047883 | * | 4/2012 |

OTHER PUBLICATIONS

Brunauer, et al., "Adsorption of Gases in Multimolecular Layers", Journal of the American Chemical Society, 1938, 60, p. 309-319.
Kroto, et al., "C60: Buckminsterfullerene" Nature, Nov. 14, 1985, 318, 162-163.
Zhao, et al., "Triblock Copolymer Syntheses of Mesoporous Silica with Periodic 50 to 300 Angstrom Pores", Science, 1998, 279, p. 548-552.
Yoo, "Silica supported metal-doped cesium ion catalyst for methacrylic acid synthesis via condensation of propionic acid with formaldehyde", Applied Catalysis A: General, 102, 1993, p. 215-232.

* cited by examiner

*Primary Examiner* — Shailendra Kumar

(57) ABSTRACT

A method for producing α-, β-unsaturated carboxylic acid esters in high yield from reaction by-product streams via the catalytic conversion of the by-products to additional α-, β-unsaturated carboxylic acid ester product. The catalyst comprises cesium, and phosphorous as a promoter, on a porous support.

10 Claims, No Drawings

PROCESS FOR PRODUCTION OF METHACRYLIC ACID ESTERS

CROSS-REFERENCE TO RELATED APPLICATIONS

This application is a 371 of PCT/US2013/041970, filed May 21, 2013, which claims priority from provisional application Ser. No. 61/655,175, filed Jun. 4, 2012, which is incorporated herein by reference in its entirety.

BACKGROUND OF THE INVENTION

The invention relates to a process for producing α-, β-unsaturated carboxylic acid esters.

U.S. Pat. No. 4,529,816 describes a conventional acetone cyanohydrin ("ACH") process for the production of methyl methacrylate ("MMA") from acetone cyanohydrin. In this process, ACH is hydrolyzed by sulfuric acid to produce α-hydroxyisobutyramide ("HIBAM") and α-sulfatoisobutyramide ("SIBAM"). Next, the HIBAM and SIBAM are thermally converted to 2-methacrylamide ("MAM") and a small amount of methacrylic acid ("MAA"). The MAM is esterified with methanol to produce the desired MMA product, while residual HIBAM is esterified to methyl α-hydroxyisobutyrate ("α-MOB"). The esterification product stream is a mixed product which is subjected to separation and purification steps to isolate the MMA product from the other compounds. Typically, a purified MMA product stream is produced, along with a purification residue comprising other compounds including, but not limited to, α-MOB and methyl β-methoxyisobutyrate (β-MEMOB). The recovery and conversion of one or more of these other compounds to produce additional MMA product has been the subject of various research and development efforts having varying degrees of success and practical utility. In particular, U.S. Pat. No. 4,529,816 describes an improvement wherein the α-MOB is isolated and recycled to the process between the thermal conversion and esterification steps.

U.S. Pat. No. 5,393,918 describes a process similar to that of U.S. Pat. No. 4,529,816, but the thermal conversion step is eliminated. Instead, the hydrolysis product is subjected directly to esterification with methanol to produce an esterification product which includes the desired MMA product, as well as α-MOB and β-MEMOB. In the process described in U.S. Pat. No. 5,393,918, the esterification ("crude MMA") product is subjected to distillation to recover the product MMA and produces a liquid residue stream comprising α-MOB and β-MEMOB. The α-MOB and β-MEMOB are separated from the residue stream, typically by fractional distillation. The recovered α-MOB and β-MEMOB are subjected to vapor phase catalytic dehydration, using a crystalline aluminosilicate, to produce a recycle mixture comprising MMA, MAA, methanol and water, which mixture is recycled to the process between the hydrolysis and esterification steps, or between the esterification and separation steps. The crystalline aluminosilicate catalyst, may be promoted with an alkali metal or a platinum group element.

Catalysts containing Cs and silica gels have been explored for a number of reactions, including dehydrations, aldol condensations and Michael additions. EP 0 545 318 and U.S. Pat. Nos. 4,841,060 and 5,625,076, for example, disclose catalysts containing silicon and at least one element selected form the group consisting of alkali metals and alkaline earth metals for intramolecular dehydrations, such as mercaptoalkanols to alkylene sulfides, alkanolamines to cyclic amines, N-(2-hydroxyethyl)-2-pyrrolidone to N-vinyl-2-pyrrolidone, and tertiary N-(2-hydroxyalkyl) carboxylic acid amide to tertiary N-alkenyl carboxylic acid amide. The substrates and reactions involved in these processes, however, differ chemically from dehydration and demethanolation of α-MOB and β-MEMOB, respectively, to MMA. U.S. 2002/0055650 discloses a process for preparing methacrylates by reacting α-hydroxy-isobutyric acid or its esters with an alcoholic compound in the presence of a catalyst comprising cesium on a support.

U.S. Pat. No. 4,801,571 discloses a process for the production of α, β-ethylenically unsaturated monocarboxylic acids, using a supported $SiO_2$—$SnO_2$ mixed oxide catalyst containing Cs, by aldol condensation of formaldehyde with, for example, propionic acid. Silica supports modified with Bi, Ti, and Ge were investigated. Catalysts prepared with these materials generally performed poorly or had unacceptably short lifetimes.

U.S. Pat. No. 6,544,924 discloses a catalytic process for the production of ethylenically unsaturated acids or esters, such as methyl methacrylate, by aldol condensation of formaldehyde with methyl propionate. The catalyst contains a porous high surface area silica, an alkali metal and at least one modifier element selected from B, Mg, Zr, Al, Mg, and Hf.

It would be desirable to have an improved process for the conversion of α-MOB and β-MEMOB to MMA.

SUMMARY OF THE INVENTION

The invention is such a process comprising contacting a $C_1$-$C_{12}$ alkyl α-hydroxyisobutyrate, a $C_1$-$C_{12}$ alkyl β-$C_1$-$C_{12}$ alkoxyisobutyrate and a $C_1$-$C_{12}$ alkyl alcohol with a supported catalyst, the catalyst comprising cesium and a phosphate promoter, under reaction conditions sufficient to convert the $C_1$-$C_{12}$ alkyl α-hydroxyisobutyrate and $C_1$-$C_{12}$ alkyl β-$C_1$-$C_{12}$ alkoxyisobutyrate to a $C_1$-$C_{12}$ alkyl methacrylate.

Surprisingly, the process can convert α-MOB and β-MEMOB to MMA with unexpectedly low amounts of methyl isobutyrate (MIB) by-product.

DETAILED DESCRIPTION OF THE INVENTION

The process of the invention involves contacting a $C_1$-$C_{12}$ alkyl α-hydroxyisobutyrate, a $C_1$-$C_{12}$ alkyl β-$C_1$-$C_{12}$ alkoxyisobutyrate and a C1-C12 alkyl alcohol with a catalyst, the catalyst comprising cesium and a phosphate promoter, under reaction conditions sufficient to convert the $C_1$-$C_{12}$ alkyl α-hydroxyisobutyrate and $C_1$-$C_{12}$ alkyl β-$C_1$-$C_{12}$ alkoxyisobutyrate to $C_1$-$C_{12}$ alkyl methacrylate.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth) acrylic acid" refers to either acrylic acid or methacrylic acid.

The terms "average pore diameter" (APD) and "average pore size" mean average pore diameter as calculated using the following Wheeler's formula: APD=4,000*(PV/SA), wherein APD is in nm, PV is pore volume (ml/g) and SA is BET surface area (m$^2$/g). Surface area and pore volume are determined using the well-known BET nitrogen adsorption/desorption method. See, e.g., S. Brunauer et al., *J.A.C.S.*, 60, 309 (1938).

The process of the invention converts certain compounds, which include at a minimum a $C_1$-$C_{12}$ alkyl α-hydroxyisobutyrate and a $C_1$-$C_{12}$ alkyl β-$C_1$-$C_{12}$ alkoxyisobutyrate, and which can comprise a mixture of by-product species, to the corresponding $C_1$-$C_{12}$ alkyl methacrylates. For example, a stream enriched in by-products may be obtained by distillation of a residue stream and can be subjected to the vapor phase catalytic reaction process described herein. Processes for the production of suitable by-product starting material mixtures are well known to those skilled in the art. For example, see the teachings of WO 2012/047883.

In one embodiment of the invention, the by-product starting materials are found in the organic fraction that is formed in a process comprising the following steps:

(a) Hydrolyze acetone cyanohydrin (ACH) with sulfuric acid to produce a hydrolysis mixture comprising 2-methacrylamide, α-sulfatoisobutyramide, α-hydroxyisobutyramide, and methacrylic acid.

(b) Esterify the hydrolysis mixture with a $C_1$-$C_{12}$ alkyl alcohol to produce an esterification mixture comprising a $C_1$-$C_{12}$ alkyl methacrylate, a $C_1$-$C_{12}$ alkyl α-hydroxyisobutyrate and $C_1$-$C_{12}$ alkyl β-$C_1$-$C_{12}$ alkoxyisobutyrate.

(c) Separate the esterification mixture into an aqueous fraction and an organic fraction comprising $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate.

In one embodiment, ACH is hydrolyzed in step (a) using excess sulfuric acid at a temperature from about 80° C. to about 135° C., preferably from about 80° C. to about 105° C., for a time sufficient to maximize the pre-esterification yield of the total of MAM, SIBAM, HIBAM, and MAA. The temperature can be maintained at a single value or changed during the course of the reaction. This may be accomplished either continuously or stepwise. The time required will vary from less than 1 minute to about 60 minutes and a hydrolysis mixture will be produced comprising MAM, SIBAM, HIBAM, and MAA. Sulfuric acid solution concentrations of 95-100% or more are preferred, but 100% or higher, e.g. oleum, sulfuric acid is not required. The mole percent distribution of reacted ACH equivalent products in the resulting hydrolysis mixture will vary. However, conditions are preferred which result in the following composition: about 60-80% MAM; about 1-20% SIBAM; about 2-20% HIBAM (more preferably 5-15%); and about 0-5% MAA with an overall ACH conversion rate of about 100%.

In this embodiment, the esterifying step (b) produces an esterification mixture comprising MMA, α-MOB, and β-MEMOB along with significant quantities of water and unreacted methanol. The esterification mixture may also include other compounds, such as MAA and β-MOB. This mixture advantageously is subjected to one or more separation and/or purification steps in step (c), comprising the use of one or more distillation columns, to remove excess methanol, water, and light impurities, such as, without limitation, dimethyl ether. Generally, liquid bottoms residue from at least one of the aforementioned distillation steps is further separated into an aqueous fraction and an organic fraction. For example, without limitation, fractional distillation conditions may be adjusted in a first distillation column to give a forerun of low boiling components such as water, unreacted methanol, small amounts of MMA, and the like, and a bottoms stream rich in MMA and other higher boiling components such as α-MOB and β-MEMOB. Furthermore, the bottoms stream may be subjected to one or more further fractional distillation steps to produce a product grade MMA stream, and a product column bottoms stream comprising MMA, as well as α-MOB, β-MEMOB, MAM, MAA, etc. suitable for use as the by-product starting material for the process of the invention.

The organic fraction of step (c) can be employed as the by-product starting material for the process of the invention. The organic fraction can be produced by distillation, in which case the process of the invention converts distillation residue species to MMA. The organic fraction of step (c), at a minimum, comprises $C_1$-$C_{12}$ alkyl methacrylate, $C_1$-$C_{12}$ alkyl α-hydroxyisobutyrate and $C_1$-$C_{12}$ alkyl β-$C_1$-$C_{12}$ alkoxyisobutyrate. For example, the $C_1$-$C_{12}$ alkyl methacrylate may be MMA, the $C_1$-$C_{12}$ alkyl α-hydroxyisobutyrate may be α-MOB, the $C_1$-$C_{12}$ alkyl β-$C_1$-$C_{12}$ alkoxyisobutyrate may be β-MEMOB, and in this case the organic fraction comprises the MMA, α-MOB and β-MEMOB. The organic fraction may also comprise organic acids such as, for example, MAA.

Depending on the configuration of the process equipment, the organic fraction may contain varying amounts of $C_1$-$C_{12}$ alkyl methacrylate. For example, in one embodiment, the organic fraction may comprise from 20 to 70 weight percent of $C_1$-$C_{12}$ alkyl methacrylate, while in another, the organic fraction may comprise from 0 to 5, or 0 to 10, weight percent of $C_1$-$C_{12}$ alkyl methacrylate.

The $C_1$-$C_{12}$ alkyl alcohol reactant preferably is methanol. Generally, the use of $C_1$-$C_4$ alcohols, such as any of methanol, ethanol, n-propanol, isopropanol, n-butanol, and isobutanol, is most common because of the commercial value of the resulting methacrylate esters. Advantageously, the alcohol is employed in an amount sufficient to maintain a relatively high ratio of MMA to MAA in the reactor product stream. Preferably, the weight ratio of alcohol to organic fraction fed to the reactor is from 0.2 to 2. Mixtures of alcohols can be employed.

The process of the invention employs a catalyst comprising cesium. The cesium may be in any form suitable for use as a catalyst under the conditions in the reactor, e.g. it may be present as a compound of cesium and another element. In one embodiment of the invention, the cesium of the catalyst may be present as a metal oxide, hydroxide or carbonate. The cesium is employed in a catalytic amount. In one embodiment of the invention, the amount of Cs, measured as cesium oxide, is from 1 to 20 weight percent, based on the total weight of the catalyst including the support. In another embodiment, the amount of Cs is from 2.5 to 15 weight percent.

The catalyst also comprises a phosphorus promoter. The promoter may be in any form suitable for use as a promoter, e.g. it may be present as a compound of phosphorus and another element. The phosphorus is employed in an amount sufficient to promote the desired reaction(s). In one embodiment of the invention, the amount of P is from 0.1 to 5 weight percent, based on the total weight of the catalyst including the support. In another embodiment, the amount of P is from 0.3 to 2 weight percent.

Furthermore, the catalyst preferably comprises a porous support material having pore openings of at least 1 nanometer. Advantageously, the average pore size of the support is from 1 to 50 nm, preferably is from 2 to 10 nm, more preferably is from 3 to 6 nm, and most preferably is from 4 to 6 nm. The porous support can be selected from a variety of commercially available inorganic carriers, such as silica gel, fumed silica, colloidal silica, alumina, titania, and tin oxide. Combinations of support materials may be employed. A silica gel type of material is preferred due to its weak acid-base property and high surface area. Some experimental samples such as mesoporous silica and foam silica like MCM-41, SBA-15, as disclosed in the literature (Nature, 1985, 318, 162; Science, 1998, 279, 548), can also be used.

It is noted that the conversion which occurs during the contacting step involves concurrent dehydration of $C_1$-$C_{12}$ alkyl α-hydroxyisobutyrate to additional $C_1$-$C_{12}$ alkyl methacrylate, and demethanolation of $C_1$-$C_{12}$ alkyl β-$C_1$-$C_{12}$ alkoxyisobutyrate to additional $C_1$-$C_{12}$ alkyl methacrylate. Thus, by-product starting materials are simultaneously converted to desired $C_1$-$C_{12}$ alkyl methacrylate product.

In one embodiment of the invention, at least a portion of the organic fraction is subjected to vaporization, along with a $C_1$-$C_{12}$ alkyl alcohol co-feed, such as, for example, without limitation, in a vaporizer, to produce a vapor feed stream comprising MMA, α-MOB, and β-MEMOB. The $C_1$-$C_{12}$ alkyl alcohol of the co-feed may be the same or different from the $C_1$-$C_{12}$ alkyl alcohol introduced in the esterifying step.

The vaporization step, involving vaporizing the alcohol co-feed and at least a portion of the organic fraction, is accomplished by vaporizing, together or separately, the co-feed and at least a portion of the organic fraction. The vaporization may be performed in any apparatus suitable for vaporizing process streams comprising the constituents discussed hereinabove including, but not limited to, flash drums, shell-and-tube heat exchangers, plate-and-frame heat exchangers, natural or forced circulation evaporators, wiped film evaporators, or combinations thereof. The particular vaporization operating conditions are selected based upon the composition of the feed stream to the vaporization and are routinely determinable by persons of ordinary skill in the relevant art to achieve the maximum recovery of desired components, while minimizing the heavies.

In one embodiment of the invention, the vaporized stream is raised to the reaction temperature in the vaporizer. Suitable, but not limiting, conditions include operating pressures and temperatures in the respective ranges of 101 to 506 kPa absolute (1 to 5 atm) and 100 to 400° C. Preferably, the pressure will be from 101 to 152 kPa absolute (1 to 1.5 atm) and the temperature will be from 250 to 360° C.

One embodiment includes conducting the vaporization as a flash distillation in a flash distillation apparatus. The flash distillation may be performed in any apparatus suitable for flash distilling process streams comprising the constituents discussed hereinabove. Suitable, but not limiting, flash distillation conditions include operating pressures and temperatures in the respective ranges of 3.33-33.3 kPa (25-250 mmHg) and 100-200° C. Preferably, the pressure is kept as low as practical, such as 6.67 kPa (50 mmHg), to maintain a low corresponding temperature, such as less than or equal to 145° C. More preferably, the flash distillation pressure is in the range of 3.33-6.67 kPa (25-50 mm Hg). More preferably, the flash distillation temperature is maintained at less than 145° C. The vapor fraction may advantageously be from 0.1 to 1.0. In one embodiment of the invention, the flash distillation is a single stage flash distillation. The bottoms stream from the flash distillation can be processed further, discarded as waste or burned as fuel.

In a preferred embodiment, the flash distillation step is operated under conditions sufficient to maximize the recovery of $C_1$-$C_{12}$ alkyl α-hydroxyisobutyrate, $C_1$-$C_{12}$ alkyl β-hydroxyisobutyrate, methacrylic acid and $C_1$-$C_{12}$ alkyl β-$C_1$-$C_{12}$ alkoxyisobutyrate, while minimizing the inclusion of methacrylamide and dimers such as, for example, dimethyl 5-methyl-2-methyleneadipate, in the flash overhead. For example, in one embodiment of the invention, a stream enriched in α-MOB, β-MEMOB, β-MOB, and MAA is obtained by a single-stage flash distillation of a residue stream and is subjected to the vapor phase catalytic reaction process described herein. The embodiment of the process that includes the flash distillation advantageously is operated in a manner that reduces fouling, reduces the buildup of heavy impurities in the recycle, reduces the organic fraction volume fed to the reactor and consequently the size of the reactor, and improves the energy efficiency and reliability of the product recovery process.

Preferably, the vapor feed stream to the reactor comprises both the vaporized co-feed and the vaporized organic feed stream. However, it is also possible to separately feed vaporized co-feed and vaporized organic feed stream to the reactor.

Preferably, the vapor feed stream to the reactor contains less than 25 wt. %, total of MAM and MMA dimer (dimethyl 5-methyl-2-methyleneadipate), based on the weight of the vapor feed stream, excluding co-feed.

Preferably, the vapor feed stream to the reactor contains less than 85 wt. % total of MAM and MMA dimer, based on the weight of MAM and MMA dimer in the stream fed to the vaporizer.

The reaction step of the process comprises contacting a vapor feed stream with a catalyst under reaction conditions sufficient to convert by-product starting materials such as, for example, α-MOB, β-MEMOB, MAA and β-MOB, to additional MMA and produce a converted mixture that comprises MMA, MAA, $C_1$-$C_{12}$ alkyl alcohol, and water. In one embodiment of the invention, the aforesaid catalytic conversion is performed in the presence of methanol and/or a diluting agent such as an inert gas, at reaction temperatures of from about 200° C. to about 400° C., preferably from 250 to 360° C. The reaction pressure is not particularly limited, and normally is equal to or slightly above atmospheric pressure for convenience of operation.

One embodiment of the invention is a method for producing methacrylic acid esters comprising contacting a vapor feed stream with a catalyst comprising cesium to convert $C_1$-$C_{12}$ alkyl α-hydroxyisobutyrate and $C_1$-$C_{12}$ alkyl β-$C_1$-$C_{12}$ alkoxyisobutyrate to additional $C_1$-$C_{12}$ alkyl methacrylate and produce a converted product mixture that comprises methacrylic acid, the $C_1$-$C_{12}$ alkyl methacrylate, $C_1$-$C_{12}$ alkyl alcohol, and water.

The product mixture from the reaction step can subjected to distillation to recover the product $C_1$-$C_{12}$ alkyl methacrylate together with some light by-products, such as $C_1$-$C_{12}$ alkyl isobutyrate and methacrylonitrile. The distillate containing the product $C_1$-$C_{12}$ alkyl methacrylate can be recycled to the process, e.g. to the hydrolysis and/or esterification steps.

Specific Embodiments of the Invention

The following examples are given to illustrate the invention and should not be construed as limiting its scope. All parts and percentages are by weight unless otherwise indicated.

EXAMPLE 1

Preparation of 10% $Cs_2O/SiO_2$ (Davisil® 636) Catalyst

A solution is prepared by dissolving 2.72 grams of cesium acetate in 75 grams of deionized water. This aqueous solution is then added into a round bottom flask containing 18 grams of silica gel having an average pore size of 60 angstroms (Davisil® Grade 636 silica gel commercially available from Aldrich). The mixture is stirred for 10 minutes and then water is removed via rotary evaporation under vacuum. The powder is further dried in a vacuum oven at room temperature overnight, followed by drying at 120° C. for 4 hours and calcining at 450° C. for 5 hours in a box furnace under air atmosphere. The calcined powder contains a nominal 10 wt. % of $Cs_2O$ and is designated 10% $Cs_2O/SiO_2$ (Davisil® 636). It is then pressed and sieved into 14-20 mesh particles prior to being loaded into a fixed bed reactor for catalytic performance evaluation.

EXAMPLE 2

Preparation of 10% $Cs_2O/SiO_2$ (Davisil® 646) Catalyst

The procedure of Example 1 is repeated except that the silica gel is Davisil® Grade 646 silica gel, having an average pore size of 150 angstroms, which is commercially available from Aldrich.

EXAMPLE 3

Preparation of 10% $Cs_2O/P/SiO_2$ (Davisil® 646) Catalyst

A solution is prepared by dissolving 2.27 g of cesium acetate in 50 g of deionized water. This solution is then added into a round bottom flask containing 15 g silica gel (Davisil® Grade 646 from Aldrich). The mixture is stirred for 10 minutes, then 1.50 g of ammonium hydrogen phosphate [$(NH_4)_2HPO_4$, from Aldrich] is added. The resulting slurry is stirred for another 10 minutes followed by rotary evaporation at room temperature under vacuum to remove the water. The resulting powder is further dried at 120° C. for 8 hours and calcined at 450° C. for 5 hours in a box furnace under an air atmosphere. It is then pressed and sieved into 14-20 mesh particles, and is designated 10% $Cs_2O/P/SiO_2$ (Davisil® 646).

EXAMPLE 4

Preparation of 10% $Cs_2O/Bi/SiO_2$ (Davisil® 636) Catalyst

A solution of 0.174 g of $Bi(NO_3)_3.5H_2O$ and 50 g of deionized water is prepared. During the preparation of the solution, 0.62 g of 5 wt. % of nitric acid in water is added to the mixture to help dissolve the bismuth nitrate salt. The mixture is stirred at room temperature and then 2.27 g of cesium acetate is added. The solution is transferred into a round bottom flask containing 15 g of silica gel (Davisil® Grade 636 from Aldrich). The mixture is stirred for 10 minutes, followed by rotary evaporation at 50° C. under vacuum to remove the water. The resulting powder is further dried at 120° C. for 5 hours and is calcined at 450° C. for 5 hours in a box furnace under an air atmosphere. It is then pressed and sieved into 14-20 mesh size particles and designated 10% $Cs_2O/Bi/SiO_2$ (Davisil® 636).

EXAMPLE 5

Preparation of 10% $Cs_2O/Zr/SiO_2$ (Davisil® 636) Catalyst

A solution of 0.58 g of zirconyl nitrate [$ZrO(NO_3)_2.xH_2O$, from Arco Organics] in 62 g of deionized water is prepared. During the preparation of the solution, 2 g of 5 wt. % of nitric acid aqueous solution is added to the mixture to help dissolve the nitrate salt. This solution is then added into a round bottom flask containing 15 g silica gel (Davisil® Grade 636 from Aldrich). The mixture is stirred for 10 minutes, followed by rotary evaporation at 50° C. under vacuum to remove the water, and is further dried in a box furnace at 120° C. for 2 hours. The dried mixture is mixed with an aqueous solution containing 50 g of water and 2.27 g of cesium acetate. The resulting slurry is put on a rotary evaporator to remove water at 50° C. under vacuum, followed with drying at 120° C. for 5 hours and calcination at 450° C. for 5 hours in a box furnace under air atmosphere. It is then pressed and sieved into 14-20 mesh size particles and designated 10% $Cs_2O/Zr/SiO_2$ (Davisil® 636).

EXAMPLE 6

Preparation of 10% $Cs_2O/SiO_2$ (Merck® 10181) Catalyst

The catalyst preparation of Example 1 is repeated except that Merck® Grade 10181 (from Aldrich) is used as the silica gel. The resulting calcined powder contains a nominal 10 wt. % of $Cs_2O$ and is pressed and sieved into 14-20 mesh size particles. It is designated 10% $Cs_2O/SiO_2$ (Merck® 10181).

EXAMPLE 7

Preparation of 10% $Cs_2O/SiO_2$ (Merck® 923) Catalyst

The catalyst preparation of Example 1 is repeated except that Merck® Grade 923 (from Aldrich) is used as the silica gel. The resulting calcined powder contains a nominal 10 wt. % of $Cs_2O$ and is pressed and sieved into 14-20 mesh size particles. It is designated 10% $Cs_2O/SiO_2$ (Merck® 923).

EXAMPLE 8

Preparation of 2.5% $Cs_2O/SiO_2$ (Merck® 10181) Catalyst

The catalyst preparation of Example 6 is repeated except that 0.68 g of cesium acetate is used. The resulting calcined powder contains a nominal 2.5 wt. % of $Cs_2O$ and is pressed and sieved into 14-20 mesh size particles. It is designated 2.5% $Cs_2O/SiO_2$ (Merck® 10181).

EXAMPLE 9

Preparation of 10% $Cs_2O/SiO_2$ (Merck® 10181, 600 C) Catalyst with Calcination at 600° C.

The catalyst preparation of Example 6 is repeated except the final calcination of the dried powder is done at 600° C. The resulting calcined powder contains a nominal 10 wt. % of $Cs_2O$ and is pressed and sieved into 14-20 mesh size particles. It is designated 10% $Cs_2O/SiO_2$ (Merck® 10181, 600 C).

EXAMPLE 10

Evaluation of the Catalyst

For each run, a catalyst of Examples 1-9 is loaded into the middle of a ½" O.D. stainless steel plug flow tubular reactor, with silicon carbide inert particles loaded above and below the catalyst charge. The amount of the catalyst varies from 1.5 g to 3.0 g. The reactor tube is installed in an electrically heated clamshell furnace. The catalyst bed is pretreated in situ by a stream of $N_2$ at 40 sccm at 360° C.-370° C. and 1 to 1.1 atmospheres pressure absolute (101.3 to 111.5 KPa) for 16-20 hours, and is then cooled to the reaction temperature, typically 300° C.-340° C.

The feed for the reaction is prepared by mixing 60 parts by weight of distillate with 40 parts by weight of methanol. The distillate is obtained by distilling heavy residue streams derived from purifying methyl methacrylate manufactured by the conventional ACH-$H_2SO_4$ route. 15 ppm of 4-methoxy phenol is added to the distillate as inhibitor. The distillation is achieved via continuous-flow fractional distillation using a 20-tray Oldershaw column. Reboiler and condenser pressures are respectively about 20.0 and 17.87 kPa (150 and 134 mmHg, respectively). Two slightly different feeds are used in the evaluation. The feed composition, as determined by gas chromatography, is listed in Table 1.

TABLE 1

Reactor feed compositions

| Feed | α-MOB | β-MEMOB | MMA | MAA | methanol |
|------|-------|---------|------|--------|----------|
| | | Component (wt. %) | | | |
| A | 43.0 | 16.35 | 0.83 | 0.036 | 39.12 |
| B | 44.94 | 12.10 | 1.24 | 0.0078 | 40.79 |

Each feed (as a single liquid mixture) is provided via syringe pump. The feed rate is 1.5 g/hr for 1.5 g of catalyst loaded, and 3.0 g/hr for 3.0 g of catalyst, in order to maintain the weight hour space velocity at 1.0 $hr^{-1}$. In most cases, $N_2$ is co-fed in a separate line at 6 SCCM. The feed is vaporized, is combined with the co-feed, and is preheated to about 160° C.-180° C. before entering the reactor tube.

The reactor temperature is varied to manipulate conversion. The single, vapor-phase reactor effluent is swept through a cold trap submerged in an ice water bath to collect condensable products, which are weighed.

Feed and product liquid stream compositions are determined by gas chromatography using two capillary columns connected in sequence (Column 1: Restek Rtx-1, dimensions 30 meters length×0.53 mm ID×1 micrometer (μm) film thickness; Column 2: Agilent DB-FFAP, dimensions 10 m length×0.53 mm ID×1 μm film thickness) and a flame ionization detector. Reaction product vapor exiting the cold trap is analyzed using a gas chromatograph equipped with silica gel and molecular sieve columns and a thermal conductivity detector. The conversions of α-MOB and β-MEMOB are calculated by difference as follows, where $n_i$ denotes the molar flow rate of species i:

$$\alpha-MOB \text{ conversion } (\%) = 100 \times \left(1 - \frac{n^{out}_{\alpha MOB}}{n^{in}_{\alpha MOB}}\right)$$

$$\beta-MEMOB \text{ conversion } (\%) = 100 \times \left(1 - \frac{n^{out}_{\beta MEMOB}}{n^{in}_{\beta MEMOB}}\right)$$

The combined molar yield of MMA and MAA on the sum of α-MOB and β-MEMOB fed is calculated as follows:

$$MMA + MAA \text{ yield } (\%) = 100 \times \frac{(n^{out}_{MMA} - n^{in}_{MMA}) + (n^{out}_{MAA} - n^{in}_{MAA})}{n^{in}_{\alpha MOB} + n^{in}_{\beta MEMOB}}$$

Test results obtained during the first 10-30 hours time on stream are shown, along with specific reaction conditions, in Tables 2, 3 and 4. In addition to conversion and yield, the relative weight ratio of by-product MIB to MMA is shown.

TABLE 2

| | Impact of Promoters | | | | |
|---|---|---|---|---|---|
| Example # | 1 | 2 | 3 | 4 | 5 |
| Catalyst | 10% $Cs_2O/$ $SiO_2$ (Davisil® 636) | 10% $Cs_2O/$ $SiO_2$ (Davisil® 646) | 10% $Cs_2O/P/$ $SiO_2$ (Davisil® 646) | 10% $Cs_2O/Bi/$ $SiO_2$ (Davisil® 636) | 10% $Cs_2O/Zr/$ $SiO_2$ (Davisil® 636) |
| Promoter element | none | none | P | Bi | Zr |
| Feed #, feed rate | A, 3.0 g/hr | A, 3.0 g/hr | A, 3.0 g/hr | B, 1.5 g/hr | B, 1.5 g/hr |
| $N_2$ co-feed (SCCM) | 6 | 6 | 6 | 0 | 6 |
| Reaction conditions* R.T. | 311° C. | 327° C. | 317° C. | 330° C. | 320° C. |
| TOS | 11 | 28 | 10 | 20 | 20 |
| Conversions (%) | | | | | |
| α-MOB | 98.9 | 99.8 | 99.8 | 97.0 | 99.9 |
| β-MEMOB | 97.5 | 100 | 80.1 | 95.6 | 99.1 |
| (MMA + MAA) Yield (%) | 91.7 | 83.0 | 88.0 | 91.9 | 87.1 |

TABLE 2-continued

| Impact of Promoters | | | | | |
|---|---|---|---|---|---|
| Example # | 1 | 2 | 3 | 4 | 5 |
| MIB/MMA (*1000) | 2.09 | 5.38 | 0.43 | 3.12 | 48.2 |

*R.T. = catalyst mid-bed temperature, TOS = time on stream (hr.).

Surprisingly, the phosphate promoter significantly reduces the formation of MIB. The Zr promoter, a highly effective promoter for $Cs/SiO_2$ catalyst used in the condensation reaction between methyl propionate and formaldehyde, as reported in U.S. Pat. No. 6,544,924, substantially increases the by-product MIB in this MMA bottoms recovery process. Bi, cited in *Applied Catalysis A: General*, 102 (1993) 215-232, is an effective promoter for aldol condensation of propionic acid with formaldehyde. However, the Bi promoter is not effective in reducing the MIB by-product for this MMA bottoms recovery process.

TABLE 3

| Impact of silica support pore structures | | | | | |
|---|---|---|---|---|---|
| Example # | | 2 | 1 | 6 | 7 |
| Catalyst | | 10% $Cs_2O$/ $SiO_2$ (Davisil ® 646) | 10% $Cs_2O$/ $SiO_2$ (Davisil ® 636) | 10% $Cs_2O$/ $SiO_2$ (Merck ® 10181) | 10% $Cs_2O$/ $SiO_2$ (Merck ® 923) |
| Pore structure** of silica gel | P.V. ($cm^3/g$) | 1.15 | 0.75 | 0.68 | 0.43 |
| | P.D. (nm) | 15 | 6 | 4 | 3 |
| | S.A. ($m^2/g$) | 300 | 480 | 675 | 550 |
| Feed #, feed rate | | A, 3.0 g/hr | A, 3.0 g/hr | A, 3.0 g/hr | B, 1.5 g/hr |
| $N_2$ co-feed (SCCM) | | 6 | 6 | 6 | 6 |
| Reaction conditions* | R.T. | 327° C. | 311° C. | 325° C. | 329° C. |
| | TOS (hr.) | 28 | 11 | 17 | 19 |
| Conversions (%) | | | | | |
| α-MOB | | 99.8 | 98.9 | 99.7 | 99.9 |
| β-MEMOB | | 100 | 97.5 | 99.3 | 100 |
| (MMA + MAA) Yield (%) | | 83.0 | 91.7 | 94.5 | 86.5 |
| MIB/MMA (*1000) | | 5.38 | 2.09 | 1.47 | 3.58 |

**P.V. (pore volume), P.D. (average pore diameter), and S.A. (surface area) are from Aldrich catalog;
*R.T. = catalyst mid-bed temperature, TOS = time on stream.

Surprisingly, the silica gel support with the relatively smaller, narrow pore size distribution of 4-6 nm provided the best catalyst in reducing by-product MIB formation. The catalyst using silica gel with larger pore sizes, such as Davisil 646, displays higher MIB formation and lower yield of MMA/MAA.

TABLE 4

| Impact of Cs loading and calcination temperature | | | |
|---|---|---|---|
| Example # | 8 | 6 | 9 |
| Catalyst | 2.5% $Cs_2O$/ $SiO_2$ (Merck ® 10181) | 10% $Cs_2O$/ $SiO_2$ (Merck ® 10181) | 10% $Cs_2O$/ $SiO_2$ (Merck ® 10181, 600 C.) |
| Cs loading (wt. %) | 2.5 | 10 | 10 |
| Calcination temperature | 450° C. | 450° C. | 600° C. |
| Feed #, feed rate | A, 3.0 g/hr | A, 3.0 g/hr | A, 3.0 g/hr |
| $N_2$ co-feed (SCCM) | 6 | 6 | 6 |
| Reaction conditions* | R.T. 320° C. | 325° C. | 325° C. |
| | TOS (hr.) 13 | 17 | 11 |
| Conversions (%) | | | |
| α-MOB | 75.7 | 99.7 | 87.4 |
| β-MEMOB | 45.6 | 99.3 | 75.8 |
| (MMA + MAA) Yield (%) | 60.6 | 94.5 | 80.3 |
| MIB/MMA (*1000) | 7.52 | 1.47 | 1.92 |

*R.T. = catalyst mid-bed temperature, TOS = time on stream.

The data in Table 4 indicates that higher Cs loading renders the catalyst more active and selective in reducing the by-product MIB formation.

The data also show that a final catalyst calcination temperature of 450° C. gives a higher yield and less by-product compared to a final catalyst calcination temperature of 600° C. Higher calcination temperatures may lead to partial pore collapse of the support and/or aggregation of Cs oxides, and as a result, reduce the catalyst activity and selectivity.

What is claimed is:

1. A process comprising contacting a $C_1$-$C_{12}$ alkyl α-hydroxyisobutyrate, a $C_1$-$C_{12}$ alkyl β-$C_1$-$C_{12}$ alkoxyisobutyrate and a $C_1$-$C_{12}$ alkyl alcohol with a supported catalyst, the catalyst comprising cesium and a phosphate promoter, under reaction conditions sufficient to convert the $C_1$-$C_{12}$ alkyl α-hydroxyisobutyrate and $C_1$-$C_{12}$ alkyl β-$C_1$-$C_{12}$ alkoxyisobutyrate to a $C_1$-$C_{12}$ alkyl methacrylate.

2. The process of claim 1 wherein the contacting is in the gas phase and produces a converted mixture that comprises a $C_1$-$C_{12}$ alkyl methacrylate, methacrylic acid, $C_1$-$C_{12}$ alkyl alcohol, and water, the catalyst comprising a support comprising silica, wherein the average pore size of the support is from 1 to 50 nm.

3. The process of claim 1 wherein the average pore size of the support is from 2 to 10 nm.

4. The process of claim 1 wherein the average pore size of the support is from 3 to 6 nm.

5. The process of claim 1 wherein the average pore size of the support is from 4 to 6 nm.

6. The process of claim 1 wherein the amount of Cs is from 1 to 20 weight percent, based on the total weight of the cesium oxide and the support, and wherein the amount of P is from 0.1 to 5 weight percent, based on the total weight of the cesium oxide and the support.

7. The process of claim 1 wherein the alcohol is methanol.

8. The process of claim 1 wherein the amount of Cs is from 2.5 to 15 weight percent.

9. The process of claim 1 wherein the amount of P is from 0.3 to 2 weight percent.

10. The process of claim 1 wherein the $C_1$-$C_{12}$ alkyl α-hydroxyisobutyrate is α-MOB, the $C_1$-$C_{12}$ alkyl β-$C_1$-$C_{12}$ alkoxyisobutyrate is β-MOB, the alcohol is methanol, and the methacrylate is methyl methacrylate.

* * * * *